United States Patent [19]

Hsu et al.

[11] Patent Number: 4,564,711

[45] Date of Patent: Jan. 14, 1986

[54] HYDROFORMYLATION CATALYST AND PROCESS

[75] Inventors: Chao-Yang Hsu, Media; Paul E. Ellis, Jr., Downingtown, both of Pa.

[73] Assignee: Sun Refining And Marketing Company, Philadelphia, Pa.

[21] Appl. No.: 732,313

[22] Filed: May 9, 1985

Related U.S. Application Data

[62] Division of Ser. No. 598,935, Apr. 11, 1984.

[51] Int. Cl.$^4$ ............................................. C07C 45/50
[52] U.S. Cl. ................................... 568/454; 568/451; 502/153
[58] Field of Search ................. 568/454, 451; 502/153

[56] References Cited

U.S. PATENT DOCUMENTS

| | | | |
|---|---|---|---|
| 3,876,672 | 4/1975 | Mrowca | 260/604 HP X |
| 3,981,925 | 9/1976 | Schwager et al. | 502/162 |
| 3,996,293 | 12/1976 | Knifton et al. | 502/169 X |
| 4,101,565 | 7/1978 | Point | 502/162 |
| 4,155,939 | 5/1979 | Poist | 260/604 HF |
| 4,256,616 | 3/1981 | Hatanaka | 502/162 X |
| 4,370,258 | 1/1983 | Ogata et al. | 502/162 |
| 4,405,496 | 9/1983 | Hsu | 502/169 X |
| 4,424,380 | 1/1984 | Hsu et al. | 568/454 |

FOREIGN PATENT DOCUMENTS

56118034 9/1981 Japan .................................. 502/162

OTHER PUBLICATIONS

Kirk–Othmer, *Encyclopedia of Chemical Technology*, (Third Edition), vol. 17, Pub. by John Wiley & Sons, N.Y., NY pp. 637–653 JACS, 97,3553 (1975).
Journal of Catalysis, 45, pp. 256–267 (1976).
JCS–Chem. Comm, pp. 462–463 (1979).

*Primary Examiner*—Werren B. Lone
*Attorney, Agent, or Firm*—J. Edward Hess; Donald R. Johnson; Stanford M. Back

[57] ABSTRACT

Olefins are hydroformylated with syngas in the presence of a novel organo metallic complex catalyst to form the corresponding aldehydes at high reaction rates and improved selectivity of linear aldehydes over branched aldehydes.

The novel catalyst comprises an organo metallic complex formed from a mixture of:
(1) platinum (II) acetylacetonate;
(2) a Group IVB metal halide; and
(3) a bidentate tertiary ligand of the formula

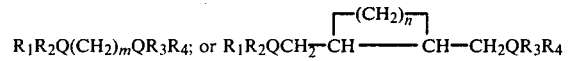

wherein Q is arsenic, antimony, or phosphorus; and $R_1$, $R_2$, $R_3$ and $R_4$ are alkyl, alkoxyl, aryl, or aryloxyl groups, and may be the same or different; and m is an integer of from 3 to about 5; and n is an integer of from 2 to about 4.

13 Claims, No Drawings

HYDROFORMYLATION CATALYST AND PROCESS

This is a division of application Ser. No. 598,935, filed Apr. 11, 1984.

BACKGROUND OF THE INVENTION

Scope of the invention

This invention relates to the process of hydroformylating olefins with syngas in the presence of a novel catalyst composition to form aldehydes. More particularly, it relates to an improved olefin hydroformylation catalyst system comprising a mixture of platinum (II) acetylacetonate; a Group IVB metal halide; and a bidentate tertiary ligand, each of which components is described in further detail below.

The novel organo metalic complex catalyst composition of this invention provides high reaction rates and high ratios of linear to branched aldehydes.

DESCRIPTION OF THE PRIOR ART

Processes of preparing aldehydes by hydroformylating an olefin with syngas, i.e., a mixture of hydrogen and carbon monoxide, in the presence of various catalysts, particularly cobalt and rhodium catalysts, is well known in the art. See, for example, Kirk-Othmer Encyclopedia of Chemical Technology ("OXO process"). Depending upon the catalyst, varying rates of reaction, and more importantly, different ratios of linear to branched aldehydes are obtained, the linear aldehydes being the preferred ones (as intermediates in the conversion, e.g., to alcohols by known hydrogenation methods and the like).

The use of platinum (II) complexes as hydroformylation catalysts in the OXO process, either alone or in combination with $SnCl_2$, is known. Higher ratios of straight to branched aldehydes are obtained when tertiary phosphine-coordinated platinum complexes are used.

For example $PtH(SnCl_3)(PPh_3)_2$ is shown by Hsu and Orchin, J. Amer. Chem Soc., 97, 353 (1975) to be useful for conversion of 1-pentene to aldehydes. Schwager and Knifton, J. Cat., 45, 256 (1976), U.S. Pat. No. 3,981,925 and U.S. Pat. No. 3,996,293 disclose use of $PtCl_2(PPh_3)_2 + SnCl_2$ for a similar reaction with 1-heptene. Kawabata, et al., J.C.S. Chem. Comm, 462 (1979) teach $Pt(PhCN)_2Cl_2 + Ph_2P(CH_2)_xPPh_2$ for conversion of 1-pentene to aldehydes. U.S. Pat. Nos. 4,101,565 and 4,155,939 show the dimer $(PtCl_2PPh_3)_2 + SnCl_2$ for hydroformylation of 1-hexene. U.S. Pat. No. 3,876,672 also shows hydroformylation of 1-hexene with $PtH(PPh_3)_3{}^+HSO_4{}^-$. See also, U.S. Pat. No. 4,405,496, which describes a platinum (acetylacetonate) in combination with a Group IVB metal halide and a tertiary phosphine. Also, U.S. Pat. No. 4,370,258 teaches the combination of platinum (II) complexed with phosphorus-, arsenic-, or antimony-containing bidentate ligands in combination with Group IVB metal halides, as hydroformylation catalysts. Other effective platinum (II) compounds include the ionic complexes shown in U.S. Pat. No. 3,876,672.

Generally speaking, however, it is recognized that platinum complexbased hydroformylation catalysts usually give slower reaction rates compared to those of the early cobalt and rhodium catalysts. It is, therefore, an object of this invention to provide an olefin hydroformylation catalyst which both gives faster reaction rates, and also maintains a high selectivity for linear over branched aldehydes.

SUMMARY OF INVENTION

In accordance with the present invention there is provided a novel olefin hydroformylation organic metallic catalyst comprising:

(1) a platinum (II) acetylacetonate [Pt (acac)$_2$];

(2) a Group IVB metal halide of the type previously used in the art but which typically has one of the following formulas:

$$MR_nX_{(4-n)}; MX_2; \text{ or } MX_4$$

wherein M is germanium, lead, or most preferably, tin; R is alkyl, aryl alkoxyl, or aryloxyl, in which case n is an integer of from 1 to 3, or R is an anion derived from a diketone, diacid, or diester, in which case n is an integer of from 1 to 3 if the anion is a mono-anion, or n is 1 if the anion is a di-anion; and x is a halide, preferably chlorine; and (3) a bidentate tertiary ligand of the formula

$$R_1R_2Q(CH_2)_mQR_3R_4; \text{ or } R_1R_2QCH_2-CH \overset{\displaystyle \lceil(CH_2)_{\overline{n}}\rceil}{\phantom{XXXX}} CH-CH_2QR_3R_4$$

wherein Q is Group VA metal, including arsenic, antimony, or preferably, phosphorus; $R_1$, $R_2$, $R_3$ and $R_4$ are alkyl, aryl, alkoxyl, or aryloxyl groups, and may be the same or different; and m is an integer of from 3 to about 5; and n is an integer of from 2 to about 4.

In the above formulas the R groups desirably contain one to six carbon atoms when alkyl, such as methyl, ethyl, or hexyl; or six to twenty carbon atoms when aryl, such as phenyl, naphthyl, tolyl or the like. Alkyl and alkoxy groups include cycloalkyl and cycloalkoxyl groups, while the aryl and aryloxyl groups include alkyl-substituted aromatic groups.

Also, the metal halides may include water of crystallization.

The invention is also directed the process of hydroformylating olefins with syngas in the presence of the aforedescribed catalysts to form aldehydes.

DESCRIPTION OF PREFERRED EMBODIMENTS OF THE CATALYST

The above-described catalyst of this invention is employed in a homogeneous system, the solvents for which may be selected from a wide range of solvents for the OXO rection such as aromatic hydrocarbons, alkylaromatic hydrocarbons; alkyl, aryl, or alkylaryl ketones; or halogenated hydrocarbons. Illustrated of specific solvents include benzene, toluene, xylenes, ethylbenzene, tetralin, acetone, methylethyl ketone, acetophenone, dichloroethane, and the like.

The catalyst complexation may be accomplished separately, but is most conveniently prepared in situ by simply mixing together in the desired solvent the three aforesaid catalyst components, and thereafter carrying out the olefin hydroformylation process in a generally known manner. When combining these components, the ratios of the components, based on their metal content, are desirably in the range of about 0.5:1 to 20:1, and preferably less than 5:1 molar ratio for the [Group IVB metal]/[Pt]; and desirably in the range of from about 1:1 to 30:1, preferably less than 5:1 for the [P]/[Pt] molar ratio.

Although the reaction system is a homogeneous one, it has been found that the catalyst may readily be recovered and recycled with little or no loss of activity.

In addition to the Pt(acac)$_2$ component, the catalyst composition includes Group IVB metal halides of the formulas defined above. Examples of these compounds which may be used in forming the catalyst of this invention include:

diphenyl tin(IV)dichloride [Sn(C$_6$H$_5$)$_2$Cl$_2$],
tin(IV)dichlorodiacetylacetonate [Sn(acac)$_2$Cl$_2$],
tin(II)dichloride [SnCl$_2$.2H$_2$O or SnCl$_2$],
tin(IV)tetrachloride [SnCl$_4$], and
phenyl tin(IV)trichloride [Sn(C$_6$H$_5$)Cl$_3$].

The third component of the catalyst complex, the bidentate tertiary ligand having the formula as defined above, include the following compounds:
trans-1,2bis (diphenylphosphinomethyl) cyclobutane (DPMCB); cis-1,2-bis (diphenylphosphinomethyl) cyclobutane; cis- and trans-1,2-bis (di-p-tolyphosphinomethyl) cyclobutane; and cis- and trans-1,2-bis (di-o-tolylphosphinomethyl) cyclobutane.

Of these DPMCB is preferred.

Illustrations of preferred combinations of the above three components used to form the catalysts complex of this invention are set forth in the examples below.

DESCRIPTION OF THE PROCESS

The hydroformylation of olefins with syngas in the presence of a catalyst is generally well-known (see the cited prior art-supra), and need not be repeated in detail herein.

Suffice it to say that the olefin starting material may be any olefin known in the art which can be hydroformylated. Examples of such olefins include C$_2$–C$_{20}$ aliphatic or cycloaliphatic monoolefins, and conjugated or non-conjugated aliphatic or cycloaliphatic diolefins which preferably are linear, but which may branched and/or substituted, including such substituted olefins as ethylenically unsaturated alcohols, aldehydes, ketones, esters and the like, as well as aromatic compounds whose ethylenically unsaturated side chain is capable of being hydroformylated, such as styrene or allylbenzene. Where mixtures of olefins are employed, the process of this invention nevertheless generally results in the selective formation of linear aldehydes in major yields.

The reaction conditions are those generally employed in the art, and may vary widely depending upon the olefin and catalyst employed, but which typcially include temperature of from about 25°–150° C., preferably 75°–105° C.; pressures of from about 100–3000 psi, preferably 750–1500 psi; and a syngas ratio of H$_2$/CO desirably in the range of from about 0.25 to 4 and more preferably 0.75 to 2.0 (molar ratio).

Finally, the concentration of catalyst complex employed in the reaction, based on the amount of metallic platinum in the complex, which may vary widely, is desirably in the range of from about $1 \times 10^{-5}$ to $1 \times 10^{-1}$ mole, and more preferably $1 \times 10^{-3}$ to $2 \times 10^{-2}$ mole, per mole of olefin present.

The hydroformylation process may be conducted in a batch, semicontinuous or continuous manner. Moreover, the process can be combined with hydrogenation of the aldehydes to alcohols by venting the reactor after aldehyde formation and introducing hydrogen under suitable conditions of temperature and pressure. The catalyst used for the hydroformylation can also be used for the hydrogenation or fresh catalyst can be added. Less preferably, the reactor is not vented and a large volume of hydrogen is introduced for admixture with syngas remaining from the hydroformylation.

The invention will now be illustrated by, but is not intended to be limited to, the following examples.

EXAMPLE 1

The following example demonstrates the utility of the catalyst of this invention in the hydroformylation of propylene to butyraldehyde.

An autoclave was charged under nitrogen atmosphere with 100 ml of p-xylene, 0.197 g (0.5 mmole) of Pt(acac)$_2$, 0.564 g (2.50 mmole) of SnCl$_2$.2H$_2$O and 0.283 g (0.625 mmole) of trans-1,2-bis (diphenylphosphinomethyl) cyclobutane (DPMCB). The autoclave was purged with syngas (H$_2$/CO=1:1) then pressured to about 400 psig with syngas and stirred for 30 min. The contents of the autoclave were then heated quickly to 80° and 10.5 g (250 mmole) of propylene was added, whereupon the total pressure was adjusted to 1500 psig by the use of a syngas reservoir. After 1 hr. of reaction, the autoclave was quickly cooled, and the liquid mixture was analyzed using vapor phase chromatography. Analytical data revealed the yield of butyraldehyde to be 99% and the ratio of n-butyraldehyde to iso-butyraldehyde was almost 15 to 1, corresponding to 93.5% of unbranched n-butyraldehyde.

EXAMPLES 2 TO 9

In these examples, summarized in Table I, the reaction procedure is similar to that shown in Example 1. Differences occur in the variation of reaction temperature and syngas (H$_2$/CO=1:1) pressure. Both higher pressure and lower temperature lead to higher normal to iso-butyraldehyde ratios. In these examples SnCl$_2$.2H$_2$O is the tin halide of choice and the diphosphine is DPMCB.

TABLE I

|  | EXAMPLE 2 | EXAMPLE 3 | EXAMPLE 4 | EXAMPLE 5 | EXAMPLE 6 | EXAMPLE 7 | EXAMPLE 8 | EXAMPLE 9 |
|---|---|---|---|---|---|---|---|---|
| REAGENTS |  |  |  |  |  |  |  |  |
| Propylene (mmole) | 259 | 259 | 246 | 260 | 258 | 258 | 255 | 259 |
| Pt(acac)$_2$ (mmole) | 0.5 | 0.5 | 0.5 | 0.5 | 0.5 | 0.5 | 0.5 | 0.5 |
| SnCl$_2$.2H$_2$O (mmole) | 2.5 | 2.5 | 2.5 | 2.5 | 2.5 | 2.5 | 2.5 | 2.5 |
| DPMCB* (mmole) | 0.63 | 0.63 | 0.63 | 0.63 | 0.63 | 0.63 | 0.63 | 0.63 |
| P-xylene (ml) | 100 | 100 | 100 | 100 | 100 | 100 | 100 | 100 |
| H$_2$/CO (1:1) (psig) | 500 | 750 | 1000 | 1250 | 1500 | 1000 | 1000 | 1000 |
| CONDITIONS |  |  |  |  |  |  |  |  |
| Temperature (°C.) | 100 | 100 | 100 | 100 | 100 | 80 | 90 | 110 |
| Reaction Time | 1 hr. | 45 min. | 30 min. | 25 min. | 25 min. | 1 hr. | 40 min. | 20 min. |
| RESULTS |  |  |  |  |  |  |  |  |
| Yield of C$_4$—Aldephydes (%) | 100 | 97 | 96 | 100 | 98 | 95 | 99 | 95 |
| Ratio of n/iso-Butyraldehyde | 83/17 | 86/14 | 88/12 | 90/10 | 91/9 | 92/8 | 90/10 | 86/14 |

TABLE I-continued

| | EXAMPLE 2 | EXAMPLE 3 | EXAMPLE 4 | EXAMPLE 5 | EXAMPLE 6 | EXAMPLE 7 | EXAMPLE 8 | EXAMPLE 9 |
|---|---|---|---|---|---|---|---|---|
| Initial Rate** | 810 | 1460 | 1990 | 2290 | 2440 | 770 | 1220 | 2450 |

*DPMCB = trans-1,2-bis(diphenylphosphinomethyl)cyclobutane
**Initial Rate = mmoles $C_4$—aldehydes/mmole Pt(acac)$_2$/hr. (calculated from first 20 min. of reaction)

EXAMPLES 10 TO 18

In these examples, summarized in Table II, the reaction procedure is similar to that utilized in Example 1. The concentration of the catalyst components has been varied as has the concentration of propylene. Again, $SnCl_2.2H_2O$ and DPMCB are the tin and diphosphine compounds of choice.

TABLE II

| | EXAMPLE 10 | EXAMPLE 11 | EXAMPLE 12 | EXAMPLE 13 | EXAMPLE 14 | EXAMPLE 15 | EXAMPLE 16 | EXAMPLE 17 | EXAMPLE 18 |
|---|---|---|---|---|---|---|---|---|---|
| REAGENTS | | | | | | | | | |
| Propylene (mmole) | 254 | 250 | 260 | 257 | 155 | 353 | 261 | 261 | 250 |
| Pt(acac)$_2$ (mmole) | 0.5 | 0.5 | 0.5 | 0.5 | 0.5 | 0.5 | 0.75 | 0.25 | 0.5 |
| SnCl$_2$.2H$_2$O (mmole) | 2.5 | 2.5 | 2.5 | 2.5 | 2.5 | 2.5 | 3.75 | 1.25 | 1.5 |
| DPMCB* (mmole) | 0.5 | 0.75 | 0.88 | 1.0 | 0.63 | 0.63 | 0.94 | 0.31 | 1.0 |
| P-xylene (ml) | 100 | 100 | 100 | 100 | 100 | 100 | 100 | 100 | 1000 |
| H$_2$/CO (1:1) (psig) | 1000 | 1000 | 1000 | 1000 | 1000 | 1000 | 1000 | 1000 | 1000 |
| CONDITIONS | | | | | | | | | |
| Temperature (°C.) | 100 | 100 | 100 | 100 | 100 | 100 | 100 | 100 | 100 |
| Reaction Time (min.) | 35 | 30 | 30 | 40 | 30 | 40 | 20 | 40 | 60 |
| RESULTS | | | | | | | | | |
| Yield of C$_4$—Aldephydes (%) | 99 | 99 | 100 | 100 | 100 | 94 | 100 | 100 | 97 |
| Ratio of n/iso-Butylraldehyde | 88/12 | 88/12 | 89/11 | 89/11 | 90/10 | 89/11 | 88/12 | 89/11 | 89/11 |
| Initial Rate** | 1280 | 1890 | 1810 | 1190 | 1390 | 1990 | 1320 | 2500 | 800 |

*DPMCB = trans-1,2-bis(diphenylphosphinomethyl)cyclobutane
**Initial Rate = mmoles $C_4$—aldehydes/mmole Pt(acac)$_2$/hr. (calculated from 20 min. of reaction)

EXAMPLES 19 TO 23

TABLE III

| | EXAMPLE 19 | EXAMPLE 20 | EXAMPLE 21 | EXAMPLE 22 | EXAMPLE 23 |
|---|---|---|---|---|---|
| REAGENTS | | | | | |
| Propylene (mmole) | 250 | 251 | 249 | 250 | 253 |
| Pt(acac)$_2$ (mmole) | 0.5 | 0.5 | 0.5 | 0.5 | 0.5 |
| DPMCB* (mmole) | 0.5 | 0.5 | 0.5 | 0.5 | 0.5 |
| SnCl$_2$.2H$_2$O (mmole) | 1.5 | 1.5 | 1.5 | 1.5 | 1.5 |
| Solvent (100 ml) | p-xylene | ethylbenzene | mixed-xylene | m-xylene | methyl isobutylketone |
| CONDITIONS | | | | | |
| Temperature (°C.) | 100 | 100 | 100 | 100 | 100 |
| Reaction Time (hr) | 1 | 1 | 1 | 1 | 1 |
| RESULTS | | | | | |
| Yield of C$_4$—Aldehydes (%) | 98 | 66 | 99 | 100 | 99 |
| Ratio of n/iso-Butyraldehyde | 88/12 | 88/12 | 89/11 | 89/11 | 87/13 |
| Initial Rate** | 1260 | 400 | 1550 | 1370 | 1050 |

*DPMCB = trans-1,2-bis(diphenylphosphinomethyl)cyclobutane
**Initial Rate = mmoles $C_4$—aldehydes/mmole Pt(acac)$_2$/hr. (calculated from first 20 min. of reaction)

EXAMPLES 24 AND 25

Using the procedure of Example 4 and substituting 2.5 mmole of $Sn(acac)_2Cl_2$ for $SnCl_2.2H_2O$ there is obtained 100% yield of C$_4$-aldehydes with 87/13 n- to iso-butyraldehyde ratio. Using the procedure of Example 4 but substituting 2.5 mmole of $Sn(C_6H_5)_2Cl_2$ for $SnCl_2.2H_2O$ gives a yield of 97% with a 89/11 n- to iso-butyraldehyde ratio.

EXAMPLE 26

In accordance with the procedures of Example 1, but substituting 1-butene for propylene, and $Sn(C_6H_5)_2Cl_2$ for $SnCl_2.2H_2O$, there is obtained linear 1-pentanal in good yield and selectivity over the corresponding branched aldehyde.

In a like manner, but substituting 1-pentene for propylene, and cis-1,2-bis (diphenylphosphinomethyl) cyclobutane for trans-DPMCB, the corresponding linear 1-hexanal is obtained in good yield and selectivity.

In accordance with the procedures of Example 1, but substituting 1-butene for propylene, and bis(1,3-diphenylphosphinopropane) for trans-DPMCB, there is obtained the corresponding linear 1-pentanal in good yield and selectively over the corresponding branched aldehyde.

EXAMPLE 27

In accordance with the procedures of Example 1, but substituting 2-pentene for propylene, $Sn(C_6H_5)Cl_3$ for SnCl$_2$.2H$_2$O, and cis-1,2-bis (di-p-tolylphosphinomethyl) cyclobutane for trans-DPMCB, there is obtained linear 1-hexanal in good yield and selectivity over the corresponding branched aldehyde.

In a like manner, but substituting styrene for propylene, and trans-1,2-bis (di-p-tolylphosphinomethyl) cyclobutane for the corresponding cis-p-tolyl compound, the corresponding 3-phenylpropanal is obtained in good yield and selectivity.

In accordance with the procedures of Example 1, but substituting 2-pentene for propylene, and bis(1,3-diphenylphosphinobutane) for trans-DPMCB, the corresponding linear 1-hexanal is obtained in good yield and selectively over the corresponding branched aldehyde.

EXAMPLE 28

In accordance with the procedures of Example 1, but substituting α-methylstyrene for propylene, SnCl$_4$ for SnCl$_2$.2H$_2$O, and cis-1,2-bis (di-o-tolylphosphinomethyl) cyclobutane for trans-DPMCB, there is obtained linear 3-phenybutyraldehyde in good yield and selectivity over the corresponding branched aldehyde.

In a like manner, but substituting allylbenzene for propylene, and trans-1,2-bis (di-o-tolylphosphinomethyl) cyclobutene for the corresponding cis-di-o-tolyl compound, the corresponding 4-phenylbutyraldehyde is obtained in good yields and selectivity.

EXAMPLE 29 (PRIOR ART)

This example illustrates the hydroformylation of propylene to butyraldehyde in the presence of a prior art platinum-phosphorus-tin complex catalyst in a manner similar to that disclosed in U.S. Pat. No. 3,981,925.

To a 300 ml stainless steel autoclave was added 100 ml of toluene as solvent, 0.53 g (1.0 mmole) of PtCl$_2$(PPh$_3$)$_2$, 1.14 g (5.0 mmole) of SnCl$_2$.2H$_2$O, and 1.31 g (5.0 mmole) of PPh$_3$. After the mixture was stirred for 15 minutes under a nitrogen atmosphere, the autoclave was purged with syngas (H$_2$/CO=1:1) and 10.5 g (250 mmole) of propylene was added. The autoclave was then charged with syngas (H$_2$/CO=1.1) to make a total pressure of 750 psig. After which the reactor was then quickly heated to 100° C. and the syngas pressure was maintained at 1000 psig through constant addition of syngas from a reservoir. After 4 hours of reaction, the autoclave was cooled to room temperature and the gas phase materials were vented. The liquid contents were removed and analyzed directly by vapor phase chromatography. Analysis of the reaction mixture indicated that 85% yield of butyraldehydes was obtained and the molar ratio of n-butyraldehydes to iso-butyraldehyde was 6.7 (i.e., 87% of normal aldehyde).

From a comparison of the results set forth in Tables I–III with those of the above prior art example, it will be seen that significant improvements have been achieved in both the rates, which are much faster, and the selectivity for linear aldehydes, which are much higher.

What we claim is:

1. In the process of hydroformylating an olefin having from about 2 to 20 carbon atoms by reacting the olefin with hydrogen and carbon monoxide at elevated pressures in the presence of a catalyst to produce an aldehyde, the improvement of using as the catalyst a catalyst system which comprises (1) a platinum (II) (acetylacetonate); (2) a Group IVB metal halide; and (3) a bidentate tertiary ligand of the formula:

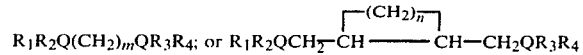

wherein Q is arsenic, antimony, or phosphorus; and R$_1$, R$_2$, R$_3$ and R$_4$ are alkyl, aryl, alkoxyl, or aryloxyl groups, and may be the same or different, m is an integer of from 3 to about 5; and n is an integer of from 2 to about 4.

2. The process of claim 1 wherein the Group IVB metal halide is of the formula:

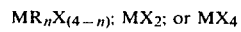

wherein M is germanium, lead, or tin; R is alkyl, aryl, alkoxy, or aryloxyl, in which case n is an integer of from 1 to 3, or R is an anion derived from a diketone, diacid, or diester, in which case n is an integer of from 1 to 3 if the anion is a mono-anion, or n is 1 if the anion is a di-anion; and X is a halide.

3. The process of claim 1 wherein the concentration of catalyst, based on the amount of metallic platinum in the complex, is from about $1 \times 10^{-5}$ to $1 \times 10^{-1}$ mole, per mole of olefin present.

4. The process of claim 1 wherein the molar ratio of the Group IVB metal to platinum is in the range of about 0.5:1 to 20:1 and the ratio of phosphorus to platinum is in the range of from about 1:1 to 30:1.

5. The process of claim 1 wherein the Group IVB metal halide is SnCl$_2$; and the bidentate tertiary ligand is trans-1,2-bis(diphenylphosphinomethyl)cyclobutane.

6. The process of claim 1 wherein the Group IVB metal halide is Sn(C$_6$H$_5$)$_2$Cl$_2$; and the bidentate tertiary ligand is trans-1,2-bis (diphenylphosphinomethyl) cyclobutane.

7. The process of claim 1 wherein the Group IVB metal halide is Sn(acetylacetonate)$_2$Cl$_2$; and the bidentate tertiary ligand is trans-1,2-bis (diphenylphosphinomethyl) cyclobutane.

8. The process of claim 1 wherein the Group IVB metal halide is Sn(C$_6$H$_5$)Cl$_3$; and the bidentate tertiary ligand is trans-1,2-bis (diphenylphosphinomethyl) cyclobutane.

9. The process of claim 1 wherein the Group IVB metal halide is SnCl$_2$; and the bidentate tertiary ligand is cis-1,2-bis (diphenylphosphinomethyl) cyclobutane.

10. The process of claim 1 wherein the Group IVB metal halide is SnCl$_2$; and the bidentate tertiary ligand is cis- or trans-1,2-bis (di-p-tolylphosphinomethyl) cyclobutane.

11. The process of claim 1 wherein the Group IVB metal halide is SnCl$_2$; and the bidentate tertiary ligand is cis- or trans-1,2-bis (di-p-tolylphosphinomethyl) cyclobutane.

12. The process according to claim 1 wherein the olefin is propylene, 1-butene, 1-pentene, 2-pentene, styrene, α-methylstyrene, or allylbenzene.

13. The process according to claim 11 wherein the olefin has from about 2 to 20 carbon atoms.

* * * * *